(12) United States Patent
Rollinger et al.

(10) Patent No.: US 9,193,658 B2
(45) Date of Patent: Nov. 24, 2015

(54) METHOD FOR REACTING GLYCERIN TO FORM ORGANIC SALTS

(71) Applicant: D.01 P.A.C. HOLDING, Wickrange (LU)

(72) Inventors: Guy Rollinger, Wickrange (LU); Armin Kempf, Wendelsheim (DE); Jindriska Maternova, Colmar-Berg (LU)

(73) Assignee: D.01 P.A.C. HOLDING, Luxembourg (LU)

( * ) Notice: Subject to any disclaimer, the term of this patent is extended or adjusted under 35 U.S.C. 154(b) by 0 days.

(21) Appl. No.: 14/398,522

(22) PCT Filed: Apr. 29, 2013

(86) PCT No.: PCT/EP2013/058875
§ 371 (c)(1),
(2) Date: Nov. 3, 2014

(87) PCT Pub. No.: WO2013/164301
PCT Pub. Date: Nov. 7, 2013

(65) Prior Publication Data
US 2015/0094489 A1    Apr. 2, 2015

(30) Foreign Application Priority Data
May 3, 2012   (LU) .......................................... 91993

(51) Int. Cl.
| | |
|---|---|
| C07C 51/41 | (2006.01) |
| C07C 53/10 | (2006.01) |
| C07C 55/06 | (2006.01) |
| C07C 59/08 | (2006.01) |
| C07C 51/16 | (2006.01) |
| C07C 51/02 | (2006.01) |

(52) U.S. Cl.
CPC ................ *C07C 51/16* (2013.01); *C07C 51/02* (2013.01); *C07C 51/41* (2013.01); *C07C 53/10* (2013.01); *C07C 55/06* (2013.01); *C07C 59/08* (2013.01)

(58) Field of Classification Search
None
See application file for complete search history.

(56) References Cited

U.S. PATENT DOCUMENTS 7,829,740 B2    11/2010   Enomoto

FOREIGN PATENT DOCUMENTS

| CN | 101541727 A | 9/2009 |
|---|---|---|
| JP | 2005200340 A | 7/2005 |

OTHER PUBLICATIONS

Hisanori Kishida et al: "Conversion of Glycerin into Lactic Acid by Alkaline Hydrothermal Reaction" Chemistry Letters, vol. 34. No. 11 (2005), pp. 1560-1561, XP008107335.
International Search Report for corresponding application PCT/EP2013/058875 filed Apr. 29, 2013; Mail date Aug. 9, 2013.
Chinese Office Action issued Jul. 8, 2015 re: Chinese Application No. 201380023318.5; pp. 1-14; citing: U.S. Pat. No. 7,829,740 B2 and CN 101541727 A.

*Primary Examiner* — Yevegeny Valenrod
(74) *Attorney, Agent, or Firm* — Cantor Colburn LLP

(57) ABSTRACT

The invention relates to a process for reacting glycerin wherein the glycerin is reacted at temperatures above 150° C. in an aqueous, liquid solution of Me hydroxide, wherein the concentration of the Me hydroxide is greater than the saturation concentration at room temperature, wherein Me is selected from the group consisting of alkali metals and alkaline earth metals and mixtures thereof, and said reaction affords at least one salt selected from the group consisting of formate, acetate, propionate, oxalate, lactate, butyrate, valerate, citrate, adipate, succinate, malate and carbonate and mixtures thereof and hydrogen gas ($H_2$) or methane ($CH_4$) and mixtures thereof.

15 Claims, No Drawings

METHOD FOR REACTING GLYCERIN TO FORM ORGANIC SALTS

TECHNICAL FIELD

The present invention relates generally to a process for reacting glycerin in highly concentrated, liquid, aqueous solutions of metal hydroxides.

BACKGROUND

Glycerin (IUPAC glycerol, also glycerine) is the trivial name and the customary name for propane-1,2,3-triol. Glycerin can be manufactured petrochemically from propylene through the intermediate products allyl chloride and epichlorohydrin, or occurs chemically as a by-product when saponifying natural fats and oils in the synthesis of soaps. Since that time large quantities of glycerin are produced as a by-product of biodiesel manufacturing. This occurs by transesterifying mainly vegetal oils with methanol. A fat molecule (triacyl glyceride) is reacted with three molecules of methanol to afford glycerin and three fatty acid methyl esters (FAME).

Depending on the transesterification process, 100 kg of glycerin are formed per ton of biodiesel. Up to now too few commercial exploitation paths have been available for this glycerin. The traditional areas of application for glycerin in the cosmetic, food, beverage and pharmaceutical industries are largely exhausted.

Consequently, excess amounts of glycerin from biodiesel production are partially disposed of in waste water or burnt for power generation.

Alternative uses are for example biogas generation, chemical transformation into fuels and lubricants or use as a feedstuff additive.

Due to its good chemical reactivity glycerin is also a suitable raw material for the production of chemicals that would otherwise be obtained from petroleum. New glycerin-based production processes, for example for epichlorohydrin or propylene glycol, are under test and processes are under development in numerous research projects in order to open up new fields of application for glycerin as a raw material.

However, few fully developed recovery technologies exist for crude glycerin.

U.S. Pat. No. 7,829,740 B2 describes a process for the production of lactate from glycerin by subjecting the glycerin to a hydrothermal reaction under alkaline conditions.

BRIEF SUMMARY

The disclosure seeks to convert glycerin and preferably glycerin from biodiesel production into a commercially valuable product.

A process is provided for reacting glycerin wherein the glycerin is reacted at temperatures above 150° C. in an aqueous, liquid solution of Me hydroxide, wherein the concentration of the Me hydroxide is greater than the saturation concentration at room temperature, wherein Me is selected from the group consisting of alkali metals and alkaline earth metals and mixtures thereof, and said reaction affords at least one salt selected from the group consisting of formate, acetate, propionate, oxalate, lactate, butyrate, valerate, citrate, adipate, succinate, malate and carbonate and mixtures thereof and hydrogen gas ($H_2$) or methane ($CH_4$) and mixtures thereof.

The process is therefore carried out in a highly concentrated, aqueous solution of Me hydroxide at temperatures in the liquid range of the system between the melting point and boiling point, preferably close to the boiling point, wherein the concentration of the Me hydroxide is greater than the saturation concentration at room temperature.

The process is preferably conducted under a pressure of 800 to 1500 hPa, preferably between 950 and 1050 hPa and particularly preferably under atmospheric pressure.

NaOH or KOH or mixtures thereof are preferably used as the Me hydroxide.

According to a preferred embodiment, the concentration of Me hydroxide is greater than 54 wt %, preferably greater than 60 wt %, particularly preferably greater than 70 wt % and quite particularly preferably greater than 80 wt % and especially greater than 85 wt %.

The reaction is preferably conducted above 150° C., particularly preferably above 160° C. and quite particularly preferably above 180° C. and especially above 200° C.

In contrast to the process described in U.S. Pat. No. 7,829,740 B2, the process according to the invention can be operated without high pressure, as the boiling point of the solution of the highly concentrated Me hydroxide is strongly increased and is significantly higher than 100° C. Moreover, the resulting salt is at least partially separated in a direct step with the reaction without additional separation steps. Therefore the process is conducted in a significantly simpler and safer manner than the process of U.S. Pat. No. 7,829,740 B2. The high hydroxide concentration enables the process to be operated at high temperatures without high pressure because the boiling point of a highly concentrated aqueous solution of Me hydroxide is significantly higher than the boiling point of water.

The reaction is preferably conducted at temperatures at the boiling point of the hydroxide solution, wherein the boiling point increases with increasing concentration of the hydroxide solution. A reflux condenser is preferably employed in order to prevent the water from leaving the reaction vessel. The vapors formed in the course of the reaction can condense on the cooling surfaces and be returned to the reaction mixture. Running water, for example, is employed as the coolant in the reflux condenser.

In the context of the invention, "temperatures at the boiling point" are understood to mean a temperature range within 15° C., preferably within 10° C., quite particularly preferably within 7.5° C. and especially within 5° C. of the boiling point of the Me hydroxide solution.

For example, if the boiling point of the sodium hydroxide solution is 150° C., then the temperature range in the context of the invention is understood to mean 135° C. to 165° C. Furthermore, the addition of glycerin causes the boiling point to shift in an unpredictable manner as the binary material system Me hydroxide-$H_2O$ transitions into the multi-component system and by the reaction products that result from the added glycerin.

According to a preferred embodiment, the process is conducted with NaOH in the concentration range 60-80% at temperatures below 180° C. At these temperatures principally lactate is produced.

It was surprisingly found that under these conditions the lactate yield of more than 97% is much higher than outside this range. Experiments in connection with the invention have shown that e.g. at 83% NaOH and 222° C. only 10.5% lactate is formed, whereas at 67%/175° C. the lactate content of the end product is approximately 98%.

According to a second preferred embodiment, the process is conducted at temperatures between 220-260° C., preferably 235° C., and affords principally acetate, propionate or oxalate as well as their mixtures. Under atmospheric pressure and concentrations of more than 85% NaOH, preferably more than 93% NaOH, and temperatures of more than 220° C., preferably more than 260° C., principally acetate or propionate as well as their mixtures are produced.

It was surprisingly found that at these temperatures principally acetate, propionate and oxalate result and no lactate. Lactate results at lower temperatures. Experiments in connection with the invention have shown that e.g. at 235° C., 35 wt % acetate, 30 wt % propionate and 25 wt % oxalate are formed and at temperatures of 260° C., 52 wt % acetate, 42 wt % propionate form.

According to another preferred embodiment, the aqueous solution of Me hydroxide is held at temperatures close to the boiling point with continuous stirring and the glycerin is metered into the Me hydroxide solution.

The glycerin is preferably pre-heated before being metered into the Me hydroxide solution.

NaOH is particularly preferably used as the Me hydroxide.

The glycerin preferably originates from the production of biodiesel.

The process can be either continuous or even a batch process.

According to a preferred embodiment, the water that results from the conversion of the glycerin is totally or partially removed.

DETAILED DESCRIPTION

Further details and advantages of the invention can be discerned from the following detailed description of the possible embodiments of the invention based on the examples.

The conversion of glycerin with highly concentrated aqueous NaOH solutions in the concentration range ≥53 wt % NaOH was tested at temperatures close to the boiling point of the NaOH solutions. Glycerin from the production of biodiesel is preferably employed as the glycerin. However, to simplify matters, pure glycerin as well as glycerin with similar water contents to crude glycerin from the biodiesel production was employed in the experiments.

In the experiments the process included the following steps:
Solid NaOH pellets were mixed in various proportions with $H_2O$ and heated under reflux.
The maximum operating temperature is given by the boiling point of the $NaOH—H_2O$ mixture at atmospheric pressure and is concentration dependent for NaOH concentrations>50 wt % in the temperature range of ca. 140° C. to more than 300° C.
Glycerin was metered in below the surface of the stirred NaOH solution, whereupon a rapid exothermic reaction occurred. In batch processes glycerin, water and NaOH were mixed and then heated.
The sole gaseous reaction products were $H_2$ and $CH_4$ with $H_2$ contents of more than 90 vol %.
The reaction products were soda ($Na_2CO_3$) and organic sodium salts from the group consisting of formate, acetate, propionate, oxalate, lactate, butyrate, valerate, citrate, adipate, succinate and malate.
The reaction could be selectively controlled such that specific salts are preferably formed.

COMPARATIVE EXAMPLE

Batch Process Under Atmospheric Pressure and NaOH Less than 54% (Laboratory)

A saturated solution with a deposit was produced at room temperature (23° C.) by adding ca. 200 g NaOH to ca. 150 ml $H_2O$. The saturated solution containing nominally 47 wt % $H_2O$/53 wt % NaOH (as per the phase diagram in the literature) was drained off from the deposit into a multi-neck glass flask. Pure glycerin (2 ml, 99.6%) was added and the mixture was slowly heated with stirring. Before heating, the headspace was firstly evacuated and then purged with nitrogen. The generated gas was led over a Y-piece equipped with a shut-off valve through a superposed gas cooling tube to a gas meter.

The temperature of the reaction mixture was measured with an immersed thermocouple. Bubble generation began at 144° C. which must be attributed to having attained the boiling point (literature 147° C.), as no volume increase was determined with the connected gas meter. The temperature was reduced to just below the boiling point and maintained for more than 1 hour. Isolated gas bubbles could be observed with a magnifying glass, but it was not possible to determine whether they were gas from a reaction of the material or were water vapor bubbles.

Ion chromatographic analysis of the reaction mixture showed the absence of reaction products. A gas analysis was not possible because the quantity was too small.

EXAMPLE 1

Batch Process Under Atmospheric Pressure (Pilot Plant)

Solid NaOH (25 kg), water (5 kg) and glycerin (3.3 kg) in the ratios 75% NaOH/15% $H_2O$/10% glycerin were charged into a stirred reactor and mixed at room temperature under an inert gas ($N_2$). Only a part of the NaOH (max approx. 5 kg with respect to pure water) dissolved at room temperature and there resulted a sticky slurry. This inhomogeneous mixture was slowly heated up at 2° C. per minute, whereby the NaOH increasingly dissolved. The boiling point of the mixture increased as the NaOH continued to dissolve. Care was taken to ensure that the mixture did not start to boil.

A homogenous liquid mixed phase was first achieved at ca. 185° C. Before this at ca. 160° C. the first gas bubbles ($H_2$) were observed, which indicated the commencement of the desired reaction. The gas generation increased with the progressive increase in temperature. The temperature was steadily increased to 218° C. Due to the system this was the maximum temperature under normal pressure because the mixture boiled vigorously.

The reaction mixture was maintained for a further 4 hours with only moderated boiling at 215° C. The resulting gas was led through an outlet tube and cooled together with the steam in the reflux condenser.

The composition of the gas was continuously measured with a thermal conductivity cell and reached maximum values of 100 vol % hydrogen.

As the reaction time progressed a solid dispersed phase was observed to increase in the liquid reaction mixture. A sample of this suspension was suctioned off for later analysis.

Analysis for organic sodium salts was carried out by means of capillary electrophoresis. The results are shown in the Table below. The 3.3 kg of glycerin starting material yielded 4.1 kg of organic salts; the yield in terms of weight was greater than 100%. Consequently, only the carbon balance is shown in the Table, i.e. the ratio of the carbon recovered in the products (C-salts) to the total carbon in the glycerin starting material (C-glycerin).

| Sodium salt | % $C_{salt}/C_{glycerin}$ |
|---|---|
| Formate | 6.2 |
| Acetate | 26.0 |
| Propionate | 8.2 |
| Oxalate | 17.9 |
| Lactate | 12.9 |
| Others (butyrate, valerate, citrate, i.a.) | ca. 1 |

In summary, more than 70 wt % of the initial carbon is found again in the organic Na salt products, principally as the acetate and oxalate. The remainder of the initial carbon is inorganically bonded in the form of $Na_2CO_3$. The carbon content in the methane fraction was neglected and not considered in the calculation.

The conversion of the glycerin can therefore be regarded as almost complete.

EXAMPLE 2

Semi-Continuous or Fed Batch Process Under Atmospheric Pressure (Laboratory)

EXAMPLE 2a

With Less than 50 Wt % NaOH

In a glass flask were mixed NaOH (15.04 g) with water (34.34 g) and after purging with nitrogen the mixture was heated up to the boiling point in a sand bath. The mixture with a nominal Na-content of 30.45% was maintained at the boiling temperature (measured temperature with an immersed thermocouple: 119° C.), the resulting steam was condensed in a reflux condenser and the water dripped back into the solution.

Anhydrous pure glycerin (0.5 ml) was injected through a capillary below the surface of the boiling mixture. This was repeated 2 minutes later and again after 10 minutes with an amount of 1 ml. The reaction mixture was maintained at the boiling temperature for 105 minutes.

No evidence of any reaction could be observed, e.g. in the form of foaming, turbidity, etc.)

After cooling, the whole reaction mixture was analyzed by means of ion chromatography. No reaction product whatsoever was found.

EXAMPLE 2b

With More than 54 Wt % NaOH

Solid NaOH pellets (87.5 g) and distilled water (14.6 g), (corresponding to NaOH (85.7 wt %) and $H_2O$ (14.3 wt %)) were weighed into a multi-neck glass flask. The flask was purged with $N_2$ and then heated under reflux with stirring up to complete dissolution of the NaOH (ca. 220° C.). The outlet of the reflux condenser was connected to a gas meter.

The temperature was then slowly increased up to the maximum possible operating temperature at atmospheric pressure, i.e. up to the nominal 230° C. boiling point of the mixture (extrapolated from the literature), in reality measured at 243° C. (the difference is probably due to a shift in the concentration because of the water fraction that circulates in the reflux system). The temperature was measured with a thermocouple that dipped into the reaction mixture.

Once the temperature had stabilized at the boiling point, slightly pre-heated pure (99.6%, ca. 35° C.) glycerin (0.7 g) was rapidly added at ca. 1 cm below the surface of the stirred NaOH solution through a calibrated 2 ml syringe and a sealed stainless steel capillary in the neck of the glass flask.

An immediate generation of gas resulted from the addition of the glycerin. About every 10 minutes a gas sample was taken through a septum by means of a gas-tight syringe and immediately analyzed by gas chromatography. The results were ca. 96 vol % $H_2$ and 4 vol % $CH_4$.

After ca. 1 hour glycerin (1.31 g) was again added and gas samples were taken, which showed ca. 98 vol % $H_2$ and 2 vol % $CH_4$.

On adding the glycerin the immediate formation of a white solid was observed. It remained in suspension with stirring and in the course of the experiment increased the viscosity of the reaction mixture (stirring made more difficult).

The contents of the flask were later analyzed for carbonate and organic contents. $Na_2CO_3$, Na formate, Na acetate, Na propionate and Na oxalate were detected, whereby, due to the method, not all substances could be determined. The individual substances were neither isolated nor quantitatively analyzed.

EXAMPLE 3

Semi-Continuous or Fed Batch Process Under Atmospheric Pressure (Pilot Plant)

Water (20 kg) was preheated to ca. 70° C. in the stirred reactor, such that almost no water vapor was formed. NaOH was added in portions though a filling vessel and stirred, such that the increasing temperature of the solution due to the high heat of solution remained far below the boiling point of the solution and no water vapor could escape through the filling vessel. The resulting minor quantities of water vapor were condensed on a reflux condenser and absorbed by the NaOH in the filling vessel, the latter being sealed with a plastic cover. Under further stirring and portion-wise addition of NaOH up to a total quantity of 100 kg, the temperature of the mixture was successively increased by external heating of the reactor until the NaOH was completely dissolved. The liquid temperature, measured with a plurality of immersion thermocouples, lay between 180° C. and 190° C. (literature value for 83.3 wt % NaOH=185° C.). After closing the filling vessel, the contents of the reactor were heated under reflux to the boiling temperature and then held at this temperature or up to 5° C. lower than this temperature.

After purging with nitrogen pure glycerin (99.6%) was preheated to 70° C. in a feed vessel and then added through a circular nozzle ca. 25 cm below the surface of the stirred reaction mixture.

In several experimental series under analogous procedures the NaOH concentration was varied between 68 wt % and 93 wt %, the reaction temperatures between 175° C. and 270° C. and the glycerin feed rate between 0.5 kg/h and 25 kg/h.

An immediate gas generation with a rapidly increasing $H_2$ content began immediately after the addition. Volumes and gas compositions were determined in-line or analyzed by means of a gas meter and a special thermal conductivity sensor.

Various gas formation rates were measured and pointed to a sequence of a plurality of secondary reactions with the formation of different products.

After reaction times between ca. 30 and 90 minutes a maximum in hydrogen concentration was always reached that was never less than 97 vol % and even reached values of 100%. For a more precise analysis, additional gas samples were taken with a sampling container from the gas stream.

Only minor fractions of methane and traces of additional organic substances in the ppm range were found in them by gas chromatography.

The interior of the stirred reactor could be monitored visually through a sight glass, whereby in addition to the gas formation, the formation of a solid reaction product could also be observed. This was caused to float on the whole area of the surface by the gas bubbles rising from the circular nozzle and formed a loose layer of foam that became increasingly compacted into a thick cake.

After the glycerin addition was ended the temperature was maintained for at least 2 hours and a subsequent reaction with gas generation was observed. When the gas generation had almost stopped (less than 1 μmin) the reactor was purged with nitrogen, opened and the flotation product completely skimmed off.

Later analyses by means of capillary electrophoresis, ion chromatography, FTIR, XRD, TIC, TOC, TGA showed a mixture of organic sodium salts (sodium carboxylates) each in variable fractions depending on the reaction conditions. The following sodium salts were found: formate, acetate, propionate, oxalate, n-butyrate, i-butyrate, n-valerate, i-valerate, lactate, citrate, succinate, adipate and malate, as well as some other species that could not be explicitly classified with the respective detection methods. In addition, the inorganic salt $Na_2CO_3$ was found in the samples and the content was determined by acid titration.

Samples were likewise taken for analysis from the liquid melt below the floating solid. They contained qualitatively the same organic salts but in another quantitative composition.

The residual melt was then poured out and left to solidify. Here, various solid phases with different compositions crystallized out in various cooling phases at different temperatures.

The following Table shows the proportion of each Na salt in the total amount i.e. including the measured amounts in the residual melt as well as the yield, expressed as the ratio of the recovered carbon in the products (C-salts) to the total carbon in the glycerin starting material (C-glycerin).

The yields of organic sodium salts (last column) decrease with increasing temperature. The yields of Na carbonate increase at the same time. The carbon fraction missing from 100% in the last column is predominantly covered by Na carbonate.

EXAMPLE 4

Analogously to Example 3 the reactor was charged with water (20 kg) and solid NaOH (60 kg), corresponding to an NaOH concentration of 75 wt %. The liquid range for this concentration is ca. 124° C. (between melting point 71° C. and boiling point 195° C.).

The temperature was brought to 180° C., i.e. 15° C. below the boiling temperature.

After purging with nitrogen, pure glycerin (99.6%), preheated to 80° C., was added at a rate of 14 kg/h, in total 32.5 kg.

The reaction ran ca. 1⅔ hours at a constant 180° C. then, in spite of a maintained controller set point, the real temperature of the reaction mixture slowly began to fall. This can be explained by the fact that the reaction mixture is slowly diluted due to the formation of water of reaction (e.g. $C_3H_8O_3+NaOH \rightarrow CH_3CH(OH)COONa+H_2O+H_2$), the concentration of the reaction mixture initially at constant temperature shifts to the boiling line and then, with additional dilution, the boiling temperature (=theoretical maximum temperature) of the system falls.

A further reduction of the reaction temperature was counteracted by a controlled removal of condensed water (ca. 16 g/min) from the water vapor phase. For the remaining reaction time the system was held constant in this way at its boiling point of 173° C., corresponding to a normal concentration, according to the literature, of ca. 66-67 wt % NaOH.

The subsequent procedure and observations correspond to Example 3, wherein in the present case, a significantly longer secondary reaction was observed, i.e. even after 8 hours the

| T (° C.) | Formate | Acetate | Propionate | Lactate | Butyrate | iso-butyrate (% in salts) | Valerate | iso-Valerate | Oxalate | Citrate | Succinate | $C_{Salt}/C_{Glyc}$ (%) |
|---|---|---|---|---|---|---|---|---|---|---|---|---|
| 175 | 2.2 | 0.0 | 0.0 | 97.8 | 0.0 | 0.0 | 0.0 | 0.0 | 0.0 | 0.0 | 0.0 | 93.2 |
| 185 | 18.6 | 3.9 | 0.0 | 62.2 | 0.0 | 0.0 | 0.0 | 0.0 | 0.0 | 15.3 | 0.0 | 77.5 |
| 216 | 13.9 | 14.6 | 12.7 | 45.8 | 0.0 | 0.0 | 0.0 | 0.0 | 13.0 | 0.0 | 0.0 | 96.0 |
| 218 | 11.4 | 19.8 | 14.2 | 26.9 | 0.2 | 0.1 | 0.3 | 0.1 | 20.2 | 0.5 | 6.3 | 89.8 |
| 220 | 10.2 | 34.5 | 21.5 | 21.7 | 0.3 | 0.1 | 0.5 | 0.0 | 7.8 | 3.4 | 0.0 | 70.1 |
| 222 | 9.0 | 29.5 | 27.6 | 10.5 | 0.3 | 0.6 | 0.4 | 0.3 | 21.9 | 0.0 | 0.0 | 76.3 |
| 235 | 6.4 | 35.1 | 30.3 | 0.0 | 0.0 | 0.0 | 0.0 | 0.0 | 25.3 | 2.9 | 0.0 | 67.4 |
| 260 | 0.8 | 51.8 | 42.2 | 0.0 | 0.0 | 0.0 | 0.0 | 0.0 | 2.6 | 0.0 | 0.7 | 56.9 |

It is clear that the salt fractions vary with the temperature, e.g.:
The acetate fraction increases within the interval 175-260° C. from 0 wt % to about 52 wt %.
The lactate fraction decreases within the interval 175-260° C. from about 98 wt % to 0 wt %.
The formate fraction is at a maximum with ca. 19% between 180 and 200° C.

Thus the reaction temperature can be used as the control parameter for selectivity, depending on which salt is preferably intended to be produced.

In addition, the different distribution of the salts in the solid and the melt can be utilized for a selective production.

Moreover, various salts can be selectively obtained in higher purity by controlled (fractionated) crystallization of the residual melt.

formation of gas with ca. 9000 liters total volume and 99.8% hydrogen content was still not quite finished.

The solid flotation product comprised lactate, oxalate, formate and acetate in the ratio 51:25:12:1.

The residual melt comprised no oxalate but only lactate, formate and acetate in the ratio 54:11:1.

The following Table shows the total yield based on the glycerin starting material:

| Sodium salt | % $C_{salt}/C_{glycerin}$ |
|---|---|
| Formate | 7.8 |
| Acetate | 1.2 |

-continued

| Sodium salt | % $C_{salt}/C_{glycerin}$ |
|---|---|
| Oxalate | 1.8 |
| Lactate | 67.8 |

The test was ended probably before the reactions had completely terminated, as a total of only ca. 80% of the glycerin had reacted.

Presumably, the lower conversion in comparison to other tests was firstly due to the high feed rate and secondly also that the conversion during feeding did not occur at the maximum possible system temperature (=boiling temperature) and consequently also occurred with a lower reaction rate.

The invention claimed is:

1. A process for reacting glycerin wherein the glycerin is reacted at temperatures above 150° C. in an aqueous, liquid solution of Me hydroxide, wherein the concentration of the Me hydroxide is greater than the saturation concentration at room temperature, wherein Me is selected from the group consisting of alkali metals and alkaline earth metals and mixtures thereof, and said reaction affords at least one salt selected from the group consisting of formate, acetate, propionate, oxalate, lactate, butyrate, valerate, citrate, adipate, succinate, malate and carbonate and mixtures thereof and hydrogen gas ($H_2$) or methane ($CH_4$) and mixtures thereof.

2. The process for reacting glycerin according to claim 1, wherein said process is carried out under a pressure of 800 to 1500 hPa.

3. The process for reacting glycerin according to claim 1, wherein NaOH or KOH as well as mixtures thereof are employed as the Me hydroxide in the process.

4. The process for reacting glycerin according to claim 1, wherein NaOH is employed as the Me hydroxide in the process.

5. The process for reacting glycerin according to claim 1, wherein the concentration of Me hydroxide is greater than 54 wt %.

6. The process for reacting glycerin according to claim 1, wherein the process is carried out in a temperature range within 15° C.

7. The process for reacting glycerin according to claim 1, wherein the process is carried out at temperatures above 160° C. and lactate is principally produced.

8. The process for reacting glycerin according to claim 1, wherein the process is carried out at temperatures between 230-260° C., and acetate, propionate and oxalate are principally produced.

9. The process for reacting glycerin according to claim 1, wherein the aqueous solution of Me hydroxide is maintained with continuous stirring at temperatures around the boiling point and the glycerin is metered the Me hydroxide solution.

10. The process for reacting glycerin according to claim 9, wherein the glycerin is preheated before being metered into the Me hydroxide solution.

11. The process for reacting glycerin according to claim 1, wherein the glycerin used originates from the production of biodiesel.

12. The process for reacting glycerin according to claim 1, wherein the process is carried out with reflux cooling.

13. The process for reacting glycerin according to claim 1, wherein said process is a continuous process.

14. The process for reacting glycerin according to claim 1, wherein said process is a batch process.

15. The process for reacting glycerin according to claim 1, wherein the water produced by the reaction of glycerin in the process is totally or partially removed.

* * * * *